US00PP08901P

United States Patent [19]

Lewandowski et al.

[11] Patent Number: Plant 8,901

[45] Date of Patent: Sep. 20, 1994

[54] *ENKIANTHUS PERULATUS* CV. 'J. L. PENNOCK'

[75] Inventors: Rick J. Lewandowski; Paul W. Meyer; Rochelle J. Dillard, all of Philadelphia, Pa.

[73] Assignee: The Trustees of the University of Pennsylvania, Philadelphia, Pa.

[21] Appl. No.: 101,840

[22] Filed: Aug. 3, 1993

[51] Int. Cl.[5] ..... A01H 5/00

[52] U.S. Cl. ..... Plt./54.1

[58] Field of Search ..... Plt. 54.1

[56] References Cited

PUBLICATIONS

Huxley, A., et al (Eds) "*Enkianthus*" *The New RHS Dictionary of Gardening* The Stockton Press (1992) N.Y., pp. 163, 164.

*Primary Examiner*—James R. Feyrer

*Attorney, Agent, or Firm*—Synnestvedt & Lechner

[57] ABSTRACT

A new and distinct variety of *Enkianthus perulatus* plant named 'J. L. Pennock,' which is particularly characterized by its distinctive, bright red fall coloration, and which can be readily distinguished from other Enkianthus plants by its onset of fall color development about two weeks before that of other *Enkianthus perulatus* plants.

9 Drawing Sheets

BACKGROUND AND SUMMARY OF THE INVENTION

This invention relates to the discovery and asexual propagation of a new and distinct variety of *Enkianthus perulatus,* a member of the Ericaceae family and sometimes called White Enkianthus. The new plant is of unknown parentage. It was selected by Rick J. Lewandowski and Paul W. Meyer from among several seedlings growing in a cultivated research collection of *Enkianthus perulatus* plants at The Morris Arboretum of the University of Pennsylvania, Philadelphia, Pa. The new plant was selected particularly because of its distinctive fall coloration. The object of this present invention is to provide a new variety of *Enkianthus perulatus* that has highly unique characteristics which lend it to decorative autumn landscaping.

The new *Enkianthus perulatus* plant has been named 'J. L. Pennock'. 'J. L. Pennock' was first asexually propagated by softwood cuttings in 1988, at The Morris Arboretum, by the plant propagator of the arboretum, Rochelle J. Dillard. Asexual propagation has further been accomplished at the Philadelphia arboretum, and also at a nursery in West Grove, Pa. Testing has shown the 'J. L. Pennock' variety maintains its distinguishing characteristics, as hereinafter set out, over several succeeding generations through asexual propagation using softwood cuttings. *Enkianthus perulatus* 'J. L. Pennock' is an attractive shrub exhibiting white flowers which are typical of the species, and bright red fall foliage, thus making it ideal for use as an ornamental garden plant. The most celebrated feature of 'J. L. Pennock' is its distinctive fall coloration which can be readily distinguished from other Enkianthus varieties by beginning to develop its fall coloration approximately two weeks before other such plants, and retaining its fall color to the end of the duration of the fall season. The following combination of characteristics are exhibited by this new variety and further enable it to be distinguished from other *Enkianthus perulatus* varieties:

(i) a dense, symmetrical growth habit that is wider than it is tall, possessing a strongly layered appearance; whereas typical *Enkianthus perulatus* plants are about as wide as they are tall;

(ii) a slow growth rate of 3 to 6 inches per year, making this plant an excellent candidate for the small garden;

(iii) highly attractive fall coloration which, in Philadelphia, begins as early as the first week of September, its leaves turning purplish, transforming to a bright red by about the end of October, and retaining color through the fall season with those of other members of the species; whereas typical *Enkianthus perulatus* varieties begin fall coloration sometime in October, and transform to red, not bright red, by sometime in November.

BRIEF DESCRIPTION OF THE FIGURES

The accompanying drawings illustrate the new *Enkianthus perulatus* variety, 'J. L. Pennock,' as grown in Philadelphia, Pa.

DETAILED DESCRIPTION OF THE PLANT

Figure 1:
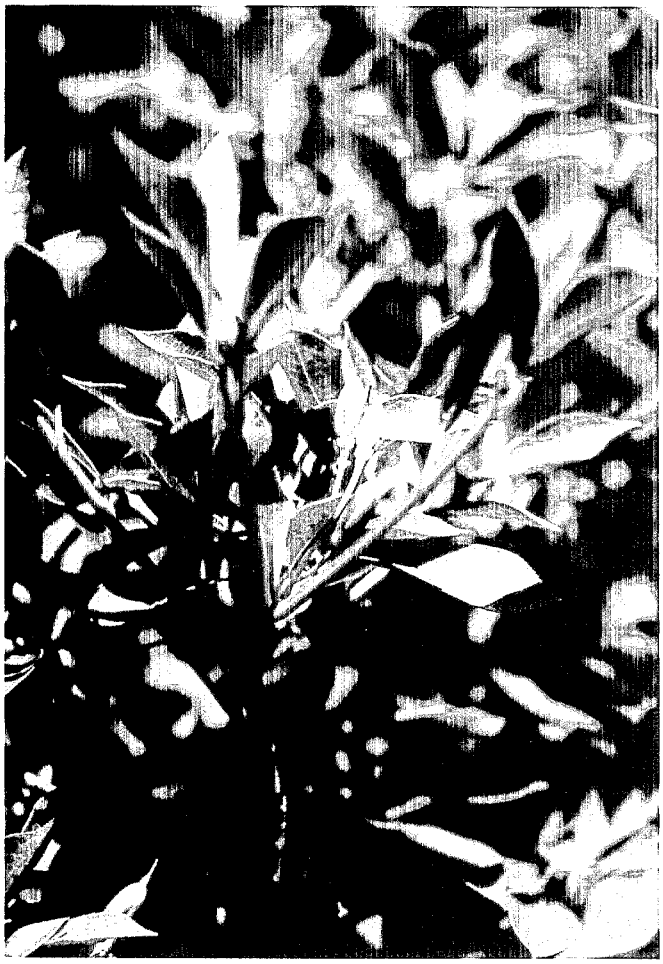
FIG. 1 is a photograph of the new *Enkianthus perulatus* 'J. L. Pennock' variety, which demonstrates the plant's winter branching habit.
Figure 2:
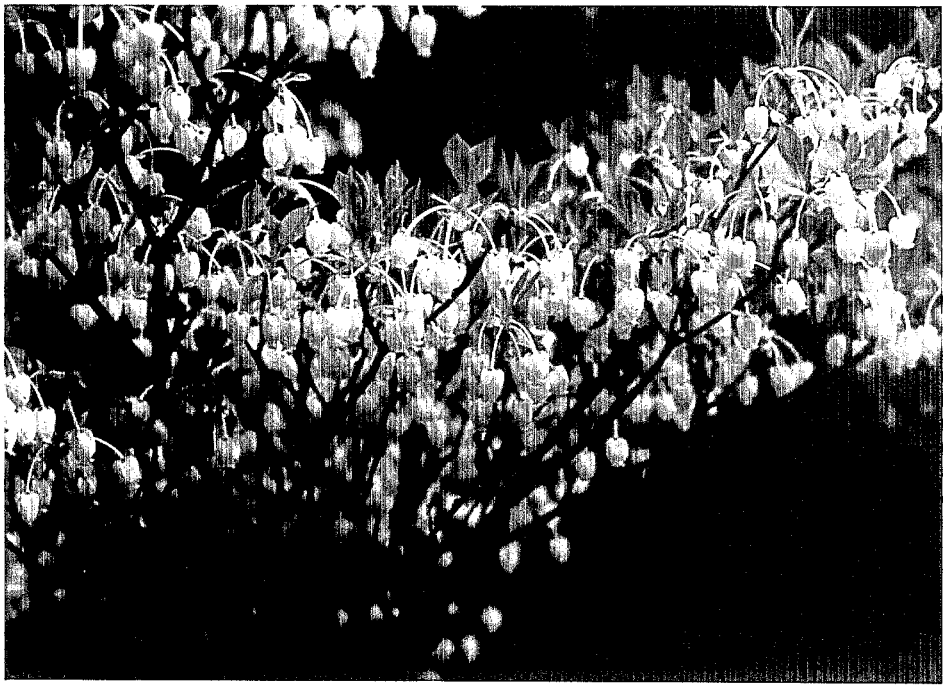
FIGS. 2 and 3 are photographs of the new *Enkianthus perulatus* 'J. L. Pennock' variety, which demonstrate the plant's summer flowering.
Figure 3:
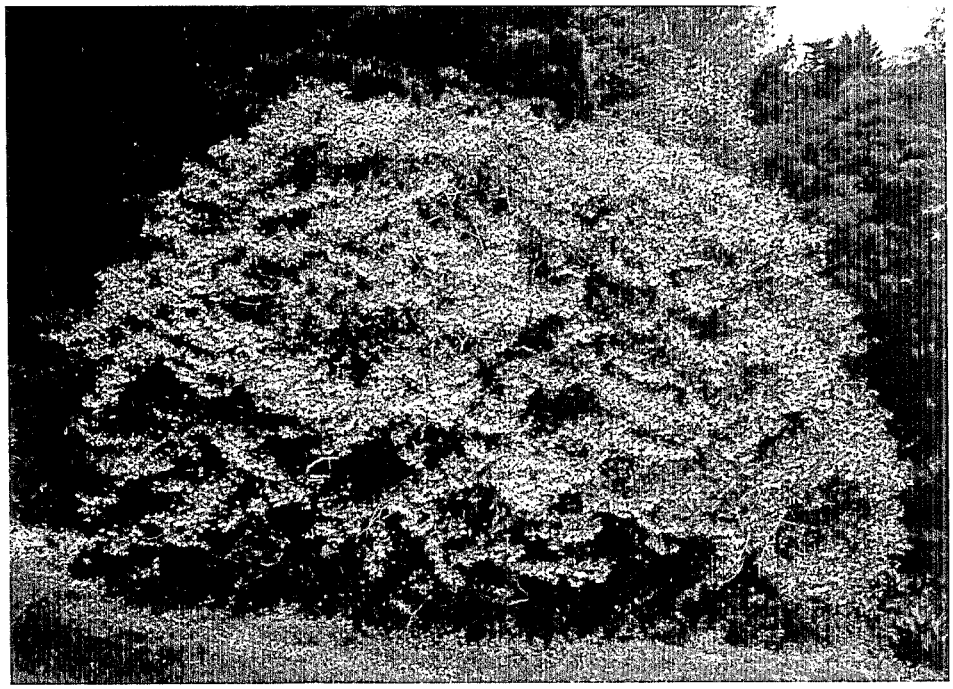
Figure 4:
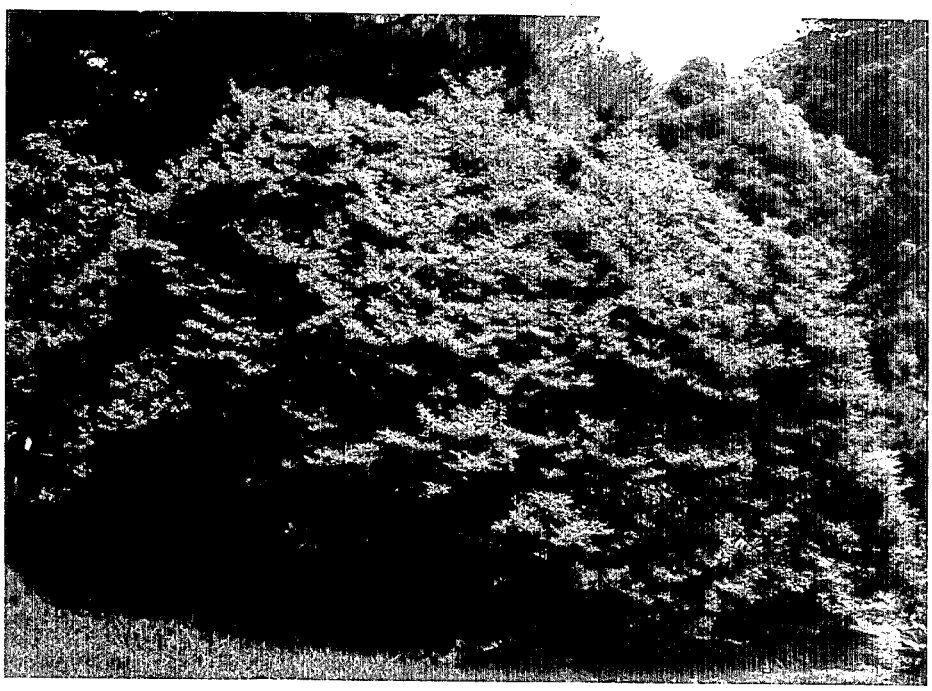
FIG. 4 is a photograph of the new *Enkianthus perulatus* 'J. L. Pennock' variety, which demostrates the plant's summer foliage.
Figure 5:
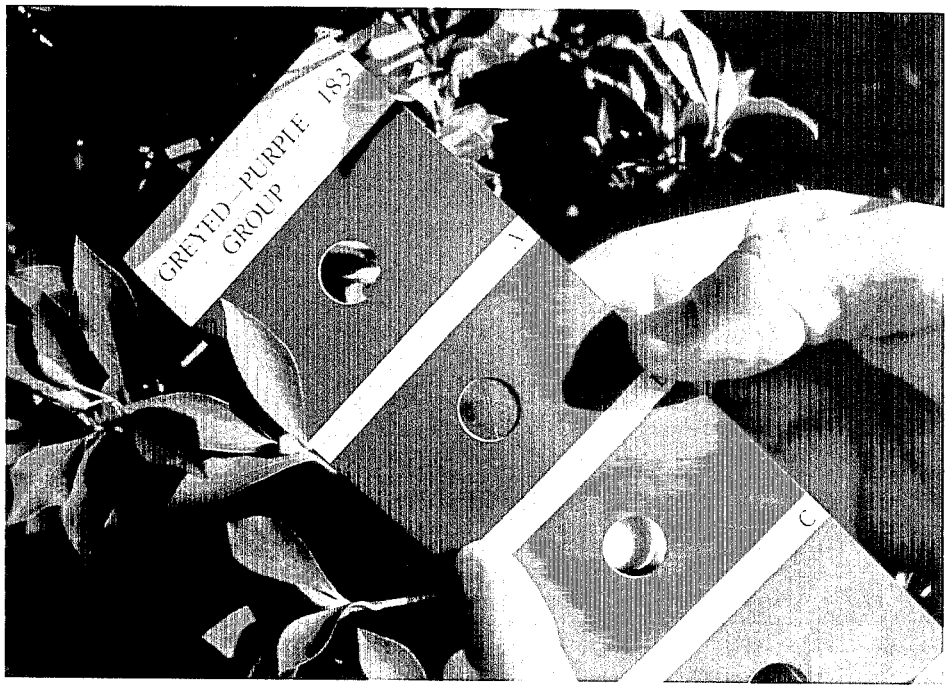
FIGS. 5 and 6 are photographs of the new *Enkianthus perulatus* 'J. L. Pennock' variety, which demonstrate the plant's foliage at an intermediate stage of fall coloration (Greyed-Purple 183-B). At this stage, which can begin as early as the first week of September, the plant no longer demonstrates its summer green foliage and has yet to demonstrate its peak autumn color, a bright red, which is fully developed by the end of October.
Figure 6:
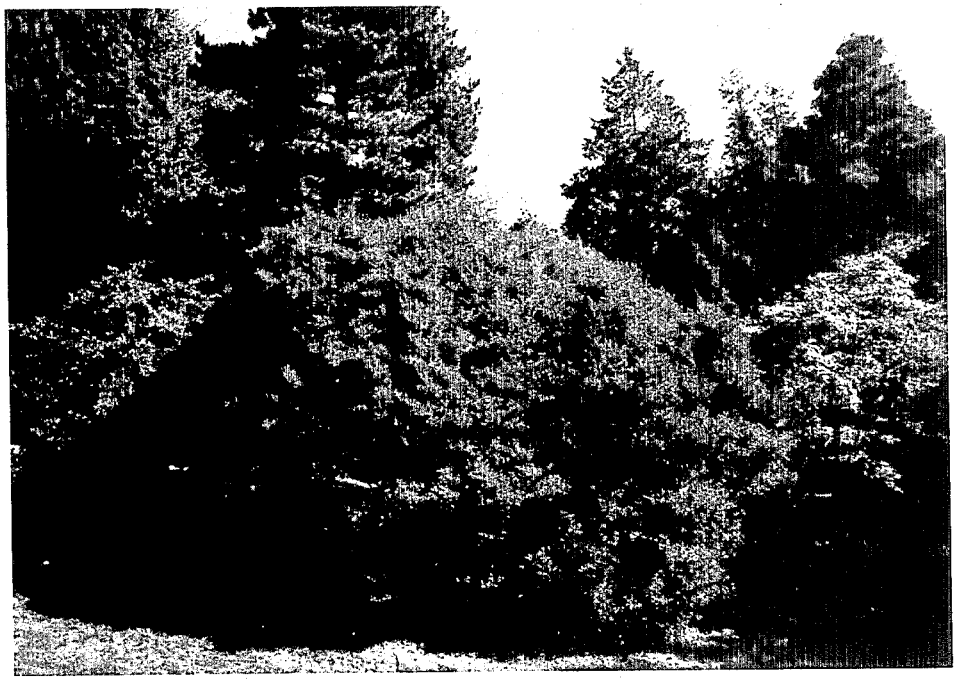
Figure 7:
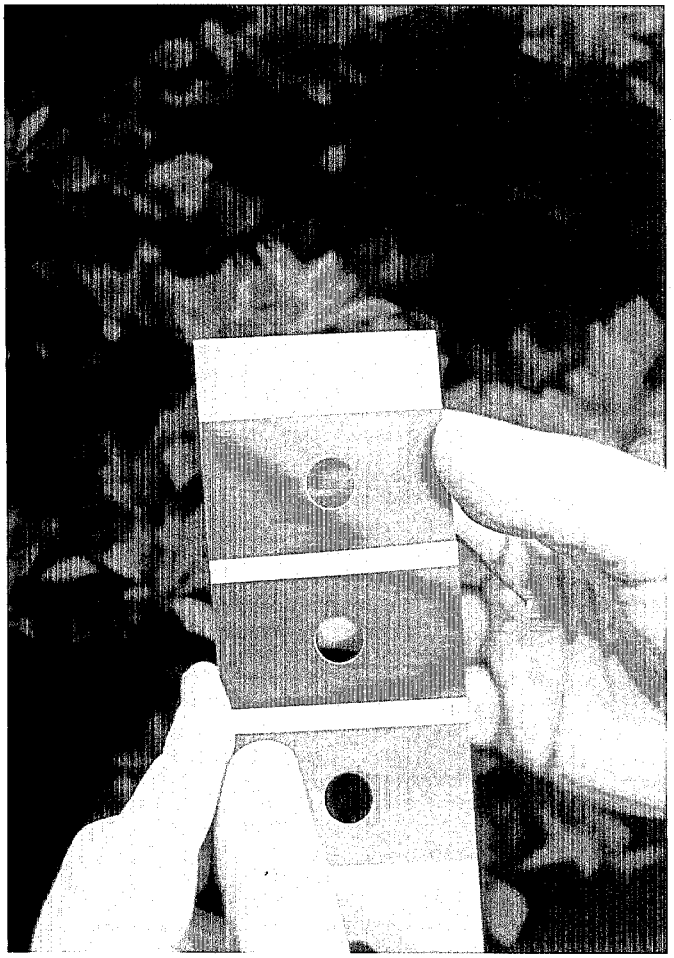
FIGS. 7 and 8 are photographs of the new *Enkianthus perulatus* 'J. L. Pennock' variety, which demonstrate the plant's foliage at its peak autumn coloration (Red 46-A).
Figure 8:
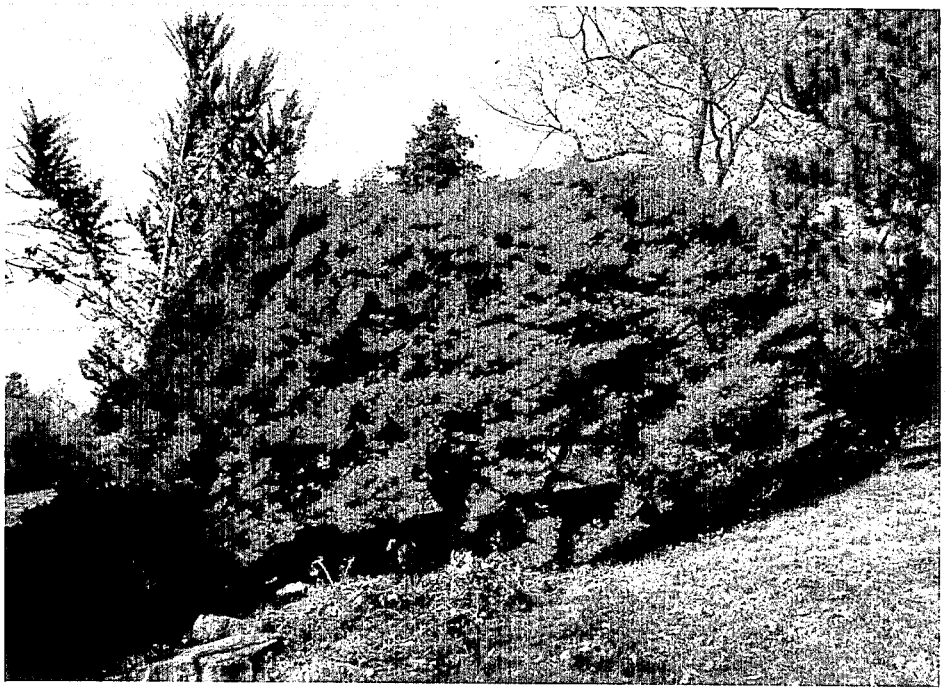
Figure 9:
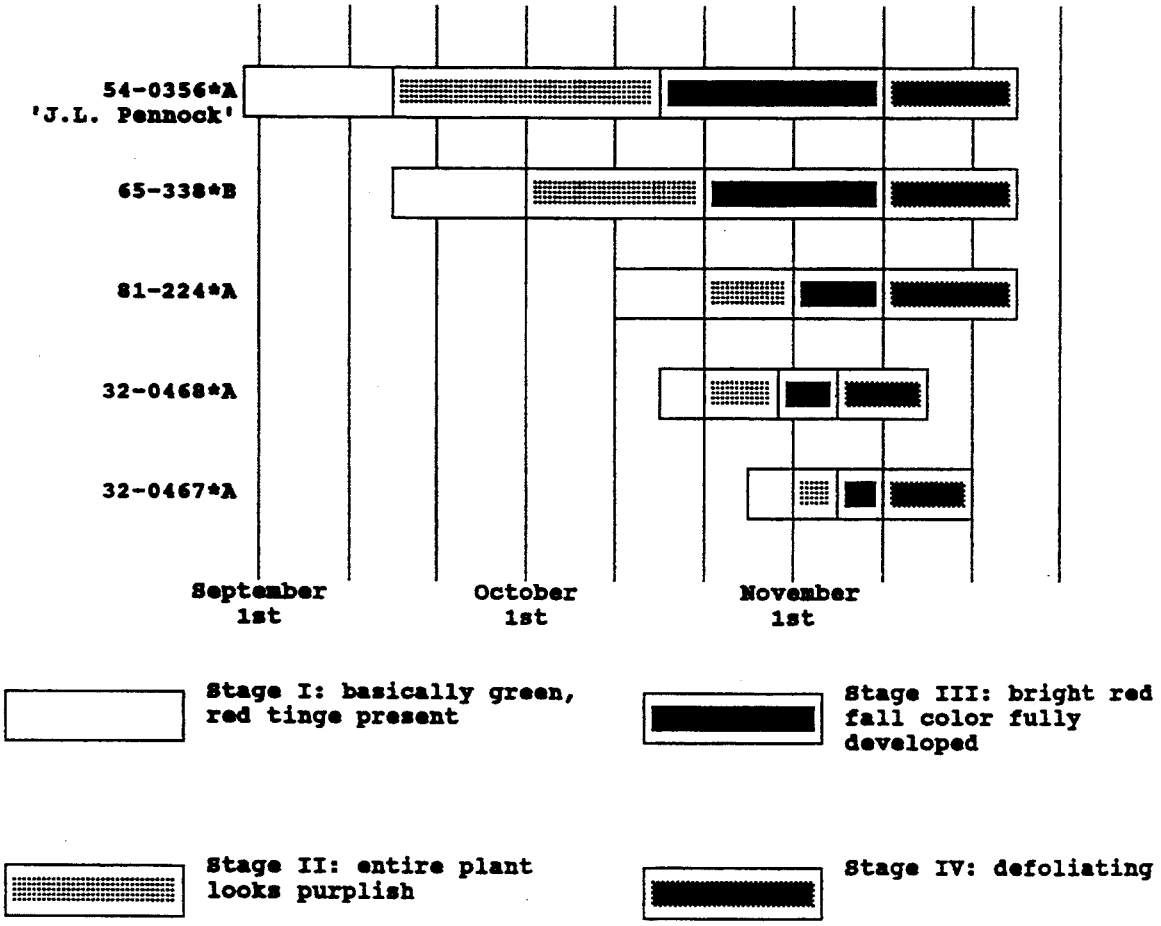
FIG. 9 is a graphic depiction of the fall color development of several *Enkianthus perulatus* plants growing at the Philadelphia arboretum in 1992. The chart clearly shows the favorable characteristics of the new 'J. L. Pennock' plant. At the fall color development Stage II, the plant begins to have an effective foliage display in landscape. As shown in the chart, 'J. L. Pennock' reaches this point about two weeks earlier than other Enkianthus plants at the arboretum, i.e. plants designated 65-338 B, 81-224 A, 32-0468 A, and 32-0467 A. 'J. L. Pennock' also reaches development Stage III about five days earlier than others. At this point, most leaves lose chlorophyll and turn to a clear, bright red (Red 45-A - 46-A). The 'J. L. Pennock' plant retains fully-developed fall color until a hard frost hits, and defoliates, at which time it parallels other *Enkianthus perulatus* plants. The new 'J. L. Pennock' plant thus has a significantly longer period of effective fall color in the landscape.

Throughout this specification, color names beginning with a small letter signify that the name of the color, as used in common speech, is aptly descriptive. Color names beginning with a capital letter designate values based on the R.H.S. Colour Chart published by The Royal Horticultural Society of London, England.

The descriptive matter which follows pertains to the *Enkianthus perulatus* 'J. L. Pennock' plants grown at The Morris Arboretum of The University of Pennsylvania, Philadelphia, Pa., and is believed to apply to plants of the variety grown under similar conditions of soil and climate elsewhere.

Name: *Enkianthus perulatus* cv. 'J. L. Pennock'.

Parentage: Unknown; selected from among several seedlings growing in a cultivated research collection of *Enkianthus perulatus* plants.

PLANT

Internode length: Varies, depending upon age, vigor and cultural conditions; on the mature parent plant, internode length ranges from 1.0 to 7.5 cm.; on younger plants, internode length can reach 15–20 cm.

Pruning and training: Can be pruned to maintain a formal, rounded habit or be pruned to induce greater branching by periodically removing some of the stems to the ground to induce additional growth; when plant if fully mature, it is essentially self-pruning.

Growth:

*Type.*—Shrubby.

*Habit.*—Globular/rounded.

Branching habit: Basally dominant with branches presented in whorls.

Size: About 2 m. tall and about 3 m. wide, at more than 40 years old.

Density: Dense.

Stem: Young shoot pale green, with red tinge (Greyed-Purple 185-A) on portion of stem exposed to full sun, turning to gray in second year; presence of hairs on stems varies from early season to late season; glabrous in late summer.

LEAVES

Type: Deciduous, and advanced before flowering.

Shape: Obovate broadly obovate.

Size: Averaging about 30 to 35 mm. in length and about 15 mm. in width.

Color:

*Upper side.*—Dull medium green (Green 143-A).

*Underneath.*—Light green (Yellow-Green 146-B).

Fall foliage: About the first week of September, the foliage begins to turn purplish (Greyed-Purple 183-A — 185-A), later transforming to its peak autumn color, a bright red (Red 45-A — Red 46-A), by the end of October.

Brilliance of upper surface: Absent.

Incisions on the margin: Present.

Hairs at the margin: Absent.

Curvature of margin: Absent.

Cross-section of blade: Flat.

Twisting of blade: Absent.

Shape of apex: Acute.

Shape of base: Cuneate.

Grooving of nerves on upper side: Little.

Undersurface: White hairs are present along the midrib.

FLOWERS

Inflorescence:

*Number of flowers.*—Few, about 2 to 5.

*Habit.*—Flowers are produced in umbels after the leaves.

*Time of flowering.*—Third week of April - first or second week of May.

Bud:

*Attitude of scales.*—Not adpressed.

*Terminal inflorescence bud.*—Shape: elliptic.

Pedicel: About 10 to 15 mm. in length.

Calyx:

*Presence.*—Present.

*Type.*—Not petaloid.

*Pubescence.*—Absent.

Flower:

*Attitude.*—Pendulous.

*Diameter.*—About 6 mm.

*Maximum width of open folded flower.*—About 4 mm.

*Shape.*—Urn-shape.

*Type.*—Single.

*Fragrance.*—Absent.

*Color.*—White.

*Zygomorphy.*—Absent.

Corolla:

*Incisions of corolla.*—Shallow.

*Length.*—Averaging about 5 to 6 mm.

*Lobes.*—Number: 5. Shape of apex: Curls up. Crenelation of margin: Absent. Undulation of margin: Absent. Hairs: Absent. Scales: Absent.

Stamens:

*Number.*—10.

*Pubescence.*—present.

Anthers: Prominent.

Pistil:

*Type.*—Not petaloid.

*Length in comparison with stamens.*—Longer.

Fruit: Typical of the species; produces no viable seed.

Table 1 below indicates the transformations in color of the new *Enkianthus perulatus* 'J. L. Pennock' variety during the various stages of fall color development, as grown in the Philadelphia arboretum in 1990.

TABLE 1

| Fall Color Development | Date | Appearance of Whole Plant | Outside Leaves | Inside Leaves |
|---|---|---|---|---|
| Summer Foliage | | medium green | Green 146-A | Green 137-A |
| Stage I | Sept. 4 | green with red tinge | Green 143-A Red 53-A, 46-A | Green 137-A |
| Stage II | Sept. 25 | maroon | Greyed-Purple 183-A | Green 137-A |

TABLE 1-continued

| Fall Color Development | Date | Appearance of Whole Plant | Outside Leaves | Inside Leaves |
|---|---|---|---|---|
| Stage III | Oct. 25 | red | Red 45-A–46-A | Greyed-Purple 187-B |
| Stage IV | Nov. 19 | brown tinge - burnt by frost | Red 45-A–46-A | Greyed-Purple 183-B |
| Defoliation | Nov. 26 | 70% defoliated | | |

We claim:

1. A new and distinct variety of *Enkianthus perulatus* plant named 'J. L. Pennock' as herein illustrated and described.

* * * * *